United States Patent
Kong et al.

(10) Patent No.: US 7,544,485 B2
(45) Date of Patent: Jun. 9, 2009

(54) BALDNESS RELATED GENE AND THE POLYPEPTIDE ENCODED THEREBY, AND USES

(75) Inventors: Xiangyin Kong, Shanghai (CN); Shanru Li, Shanghai (CN); Landian Hu, Shanghai (CN); Yaozhou Shi, Shanghai (CN); Xiaokun Teng, Shanghai (CN)

(73) Assignee: Shanghai Institutes for Biological Sciences CAS, Shanghai (CN)

( * ) Notice: Subject to any disclaimer, the term of this patent is extended or adjusted under 35 U.S.C. 154(b) by 239 days.

(21) Appl. No.: 10/534,894

(22) PCT Filed: Nov. 13, 2003

(86) PCT No.: PCT/CN03/00956

§ 371 (c)(1),
(2), (4) Date: May 13, 2005

(87) PCT Pub. No.: WO2004/052927

PCT Pub. Date: Jun. 24, 2004

(65) Prior Publication Data

US 2006/0039884 A1    Feb. 23, 2006

(30) Foreign Application Priority Data

Nov. 13, 2002  (CN)  ............................. 02 1 45253

(51) Int. Cl.
C12P 21/06  (2006.01)
C12N 5/00  (2006.01)
C12N 15/00  (2006.01)
C07H 21/04  (2006.01)
C07K 14/00  (2006.01)

(52) U.S. Cl. .................. 435/69.1; 435/325; 435/320.1; 536/23.5; 530/350

(58) Field of Classification Search .................. None
See application file for complete search history.

(56) References Cited

FOREIGN PATENT DOCUMENTS

| WO | WO 99/63083 | 12/1999 |
| WO | WO 00/70945 A2 | 11/2000 |
| WO | WO 2003027228 | * 4/2003 |

OTHER PUBLICATIONS

Strausberg et al. 2002 PNAS 99:16899-16903.*
Springer et al 2003. American Family Phys. 68:93-102.*
Goodman and Gilman, 10th edition, McGraw-Hill, 2001, p. 3-29.*
Ahmad et al 1998. Science 279:720-724.*
Genebank Online, accessiong No. AK042635, Sep. 19, 2003.
Genebank Online, accessiong No. AK028872, Sep. 18, 2003.

* cited by examiner

*Primary Examiner*—Manjunath N Rao
*Assistant Examiner*—Shulamith H Shafer
(74) *Attorney, Agent, or Firm*—Hamre, Schumann, Mueller & Larson, P.C.

(57) ABSTRACT

The invention has disclosed a baldness-related gene and the encoded polypeptide, and a process for producing the polypeptide by recombinant methods. It has also disclosed the use of Rhor gene and protein in the diagnosis and treatment of baldness.

8 Claims, 1 Drawing Sheet

BALDNESS RELATED GENE AND THE POLYPEPTIDE ENCODED THEREBY, AND USES

CROSS-REFERENCE TO RELATED APPLICATION

This Application is a Section 371 National Stage Application of International Application No. PCT/CN2003/000956, filed 13 Nov. 2003 and published as WO 2004/052927 A1 on 24 Jun. 2004, which claims the priority from the Chinese patent application 02145253.9, filed Nov. 13, 2002, the subject matter of which are hereby incorporated by reference in its entirety.

FIELD OF INVENTION

This invention relates to biological and medical fields. In particular, it relates to a novel polynucleotide encoding baldness-related protein and the polypeptide encoded by the polynucleotide. The invention also relates to the uses and preparation of these polynucleotides and polypeptides.

TECHNICAL BACKGROUND

The human primary baldness and loss of hair are quite common in the males, but are rare in females. Although baldness does not influence the survival of human living, it may severely influence the quality of individual life, especially for female patients suffering from this inherent genetic disease. Unfortunately, up to now, there is no way to completely cure baldness. Furthermore, it is very difficult to get the family suffering primary baldness.

Up to now, no baldness related gene has been isolated or discovered. Therefore, there is an urgent need to develop new baldness-related proteins.

SUMMARY OF INVENTION

One purpose of the invention is to provide a baldness-related protein, which was named Rhor protein, and its fragments, analogs and derivatives.

Another purpose of the invention is to provide a polynucleotide encoding said polypeptides.

Still another purpose of the invention is to provide a method for preparing said polypeptides and the uses of said polypeptides and their encoding sequences.

In the 1st aspect, the invention provides an isolated Rhor polypeptide, which comprises a polypeptide having the amino acid sequence of SEQ ID NO: 2, its conservative variants, its active fragments, and its active derivatives. Preferably, said polypeptide is a polypeptide having the amino acid sequence of SEQ ID NO: 2.

In the 2nd aspect, the invention provides an isolated polynucleotide, which comprises a nucleotide sequence sharing at least 85% homology to the following nucleotide sequence: (a) the nucleotide sequence encoding the above Rhor polypeptide; (b) the polynucleotide complementary to nucleotide sequence of (a). Preferably, said nucleotide sequence encodes a polypeptide comprising the amino acid sequence of SEQ ID NO: 2. More preferably, said polynucleotide comprises nucleotides 1-2484 of SEQ ID NO: 1.

In the 3rd aspect, the invention provides a vector comprising the above polynucleotide, and a host cell transformed with said vector or a host cell transformed with said polynucleotide.

In the 4th aspect, the invention provides a method for producing a polypeptide having the activity of Rhor protein, which comprises:
(a) culturing the above transformed host cell under the conditions suitable for the expression of protein;
(b) isolating the polypeptides having the activity of Rhor protein from the culture.

In the 5th aspect, the invention provides an antibody specifically bound to Rhor protein. Also provided are nucleic acid molecules for detection, which comprises consecutive 20-2484 nucleotides of the above polynucleotide.

In the 6th aspect, it provides compounds that simulate, promote and antagonize Rhor activity, or inhibit Rhor expression and methods for screening and preparing these compounds. Preferably, the compounds are antisense sequences of Rhor encoding sequence or fragments thereof.

In the 7th aspect, it provides a method for detecting Rhor protein in a sample, comprising: contacting the sample with the antibody specifically against Rhor protein, observing the formation of antibody complex which indicates the presence of Rhor protein in the sample.

In the 8th aspect, it provides a method for determining the diseases related to Rhor abnormal expression (e.g., baldness) or the susceptibility thereof, which comprises detecting the mutation of Rhor encoding sequence. Preferably, said mutation is deletion of nucleotides 351-580 of SEQ ID NO: 1. Further, the invention provides a kit for detecting baldness comprising the primers which specifically amplify the Rhor gene or transcript. Preferably, the kit further comprises a probe that binds to the site of mutation.

In the 9th aspect, it provides the uses of Rhor and its encoding sequence, e.g., in screening Rhor agonists and antagonist, and peptide fingerprinting. The Rhor encoding sequence and its fragment can be used as primers in PCR, or probes in hybridization and microarray.

In the 10th aspect, it provides a pharmaceutical composition comprising a safe and efficient amount of Rhor protein, or its agonist or antagonist and pharmaceutically acceptable carrier. This pharmaceutical composition can be used to treat diseases, e.g., baldness.

The other aspects of the invention will be apparent to the skilled in the art in light of the technical disclosure of the invention.

DETAILED DESCRIPTION OF INVENTION

After comprehensive and extensive study, the inventors have first isolated and identified a new gene Rhor, which is close related to baldness. Rhor gene encodes a protein similar to EGF receptor. The mutation of Rhor as well the decrease or loss of Rhor function directly result in baldness. On basis of said discovery, the inventors completed this invention.

As used herein, the term "Rhor protein", "Rhor polypeptide" or "baldness-related protein Rhor" are exchangeable, referring to a protein or polypeptide comprising the amino acid sequence of natural baldness-related peptide Rhor (SEQ ID NO: 2). The term includes Rhor protein with or without the starting Met residue, Rhor protein with or without signal peptide. The Rhor is also known as "RHBDL5"

As used herein, the term "isolated" refers to a substance which has been isolated from the original environment. For naturally occurring substance, the original environment is the natural environment. E.g., the polynucleotide and polypeptide in a naturally occurring state in the viable cells are not isolated or purified. However, if the same polynucleotide and polypeptide have been isolated from other components naturally accompanying them, they are isolated or purified.

As used herein, the terms "isolated Rhor protein or polypeptide" mean that Rhor polypeptide does not essentially contain other proteins, lipids, carbohydrate or any other substances associated therewith in nature. The artisans can purify Rhor protein by standard protein purification techniques. Essentially purified polypeptide forms a single main band on a non-reductive PAGE gel.

The polypeptide of invention may be a recombinant, natural, or synthetic polypeptide, preferably a recombinant polypeptide. The polypeptide of invention may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the recombinant production, the polypeptide may be glycosylated or non-glycosylated.

The invention further comprises the fragments, derivatives and analogues of Rhor. As used in the invention, the terms "fragment", "derivative" and "analogue" mean the polypeptide that essentially retains the same biological functions or activity of natural Rhor protein. The fragment, derivative or analogue of the polypeptide may be (i) one in which one or more of the amino acid residues are substituted with a conserved or non-conserved amino acid residue (preferably a conserved amino acid residue), or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to mature polypeptide, such as a leader or secretary sequence or a sequence used for purifying polypeptide or proprotein, e.g., a fusion protein formed with IgC fragment. Such fragments, derivatives and analogs are known to the artisans based on the teachings herein.

In the present invention, the term "Rhor polypeptide" means a polypeptide having the activity of Rhor protein comprising the amino acid sequence of SEQ ID NO: 2. The term also comprises the variants which have the same function of Rhor. These variants include, but are not limited to, deletions, insertions and/or substitutions of several amino acids (typically 1-50, preferably 1-30, more preferably 1-20, most preferably 1-10), and addition of one or more amino acids (typically less than 20, preferably less than 10, more preferably less than 5) at C-terminal and/or N-terminal. E.g., the protein functions are usually unchanged when an amino residue is substituted by a similar or analogous one. Further, the addition of one or several amino acids at C-terminal and/or N-terminal usually does not change the protein function. The term also includes the active fragments and derivatives of Rhor protein.

The variants of polypeptide include homologous sequences, conservative mutants, allelic variants, natural mutants, induced mutants, proteins encoded by DNA which hybridizes to Rhor DNA under high or low stringency conditions as well as the polypeptides retrieved by antisera raised against Rhor polypeptide. The present invention also provides other polypeptides, e.g., fusion proteins, which include the Rhor polypeptide or fragments thereof. Besides substantially full-length polypeptide, the soluble fragments of Rhor polypeptide a re also included. Generally, these fragments comprise at least 10, typically at least 30, preferably at least 50, more preferably at least 80, and most preferably at least 100 consecutive amino acids of Rhor polypeptide.

The invention also provides the analogues of Rhor polypeptide. Analogues can differ from naturally occurring Rhor polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to glycosylation enzymes (e.g., mammalian glycosylating or deglycosylating enzymes). Also included are sequences having phosphorylated amino acid residues, e.g., phosphotyrosine, phosphoserine, phosphothronine, as well as sequences modified to improve the resistance to proteolytic degradation or to optimize solubility properties.

In the invention, "Rhor conservative mutant" means a polypeptide formed by substituting at most 10, preferably at most 8, more preferably 5, and most preferably at most 3 amino acids with the amino acids having substantially the same or similar property, as compared with the amino acid sequence of SEQ ID NO: 2. Preferably, these conservative mutants are formed by the substitution according to Table 1.

TABLE 1

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The polynucleotide of invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO:1, or is a degenerate sequence. As used herein, the term "degenerate sequence" means an sequence which encodes a protein comprising the sequence of SEQ ID NO: 2 and which has a nucleotide sequence different from the coding region in SEQ ID NO:1.

The sequences encoding the mature polypeptide include those encoding only the mature polypeptide, those encoding mature polypeptide plus various additional encoding sequence, the encoding sequence for mature polypeptide plus the non-encoding sequence and optional additional encoding sequence.

The term "polynucleotide encoding the polypeptide" includes the polynucleotide encoding said polypeptide and the polynucleotide comprising additional and/or non-encoding sequence.

The invention further relates to the variants of polynucleotides which encode a polypeptide having the same amino acid sequence, or its fragment, analogue and derivative. The variant of the polynucleotide may be a naturally occurring allelic variant or an on-naturally occurring variant. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The invention further relates to polynucleotides, which hybridize to the hereinabove-described sequences, if there is at least 50%, preferably at least 70%, and more preferably at least 80% between the sequences. The invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2×SSC, 0.1% SDS, 60° C.; (2) hybridization after adding denaturants, such as 50% (v/v) formamide, 0.1% bovine serum/0.1% Ficoll, 42° C.; or (3) hybridization of two sequences sharing at least 95%, preferably 97% homology. Further, the hybridizing polynucleotides encode a polypeptide which retains the same biological function or activity as the mature polypeptide of SEQ ID NO:2

The invention also relates to nucleic acid fragments hybridized with the hereinabove sequence. As used herein, the length of "nucleic acid fragment" is at least 15 bp, preferably 30 bp, more preferably 50 bp, and most preferably at least 100 bp. These fragments can be used in the amplification techniques of nucleic acid, e.g., PCR, to determine and/or isolate the Rhor encoding polynucleotide.

The polypeptide and polynucleotide of the invention preferably are provided in isolated form, more preferably are purified to be homogeneous.

The full-length Rhor nucleotide sequence or its fragment can be prepared by PCR amplification, recombinant method and synthetic method. For PCR amplification, one can obtain said sequences by designing primers based on the nucleotide sequence disclosed herein, especially the ORF, and using cDNA library commercially available or prepared by routine techniques in the art as a template. When the sequence is long, it is usually necessary to perform two or more PCR amplifications and link the amplified fragments together correctly.

Once the sequence is obtained, one can produce lots of the sequences by recombinant methods. Usually, said sequence is cloned into a vector which is then transformed into a host cell. The sequence is isolated from the amplified host cells using conventional techniques.

Further, the sequence can be synthesized, especially when the fragments are short. Typically, several small fragments are synthesized and linked together to obtain a long sequence.

It is completely feasible to chemically synthesize the DNA sequence encoding the protein of invention, or the fragments or derivatives thereof. In addition, the mutation can be introduced into the protein sequence by chemical synthesis.

The amplification of DNA/RNA by PCR is preferably used to obtain Rhor gene. The primers used in PCR can be properly selected according to the sequence information disclosed herein and synthesized by the conventional methods. The amplified DNA/RNA fragments can be isolated and purified by conventional methods, e.g., gel electrophoresis.

The invention further relates to a vector comprising the polynucleotide of invention, a genetic engineered host cell transformed with the vector or the sequence encoding Rhor protein, and the method for producing the Rhor polypeptide by recombinant techniques.

The recombinant Rhor polypeptides can be expressed or produced by the conventional recombinant DNA technology (Science, 1984; 224:1431), using the polynucleotide sequence of invention. Generally, it comprises the following steps:

(1) transfecting or transforming the appropriate host cells with the polynucleotide encoding Rhor polypeptide or the vector containing the polynucleotide;
(2) culturing the host cells in an appropriate medium;
(3) isolating or purifying the protein from the medium or cells.

In the present invention, the polynucleotide sequences encoding Rhor protein may be inserted into a recombinant expression vector. The term "expression vector" refers to a bacterial plasmid, bacteriophage, yeast plasmid, plant virus or mammalian cell virus, such as adenovirus, retrovirus or any other vehicle known in the art. Vectors suitable for use in the present invention include, but are not limited to, the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. On the whole, any plasmid or vector can be used to construct the recombinant expression vector as long as it can replicate and is stable in the host. One important feature of expression vector is that the expression vector typically contains an origin of replication, a promoter, a marker gene as well as the translation regulatory components.

The methods known by the artisans in the art can be used to construct an expression vector containing the DNA sequence of Rhor and appropriate transcription/translation regulatory components. These methods include in vitro recombinant DNA technique, DNA synthesis technique, in vivo recombinant technique and so on (Sambrook, et al. Molecular Cloning, a Laboratory Manual, Cold Spring Harbor Laboratory. New York, 1989). The DNA sequence is efficiently linked to the proper promoter in an expression vector to direct the synthesis of mRNA. The exemplary promoters are lac or trp promoter of E. coli; $P_L$ promoter of lamda-phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome-binding site for initiating the translation, transcription terminator and the like.

The expression vector preferably comprises one or more selective marker genes to provide a phenotype for selecting the transformed host cells, e.g., the dehydrofolate reductase, neomycin resistance gene and GFP (green fluorescent protein) for eukaryotic cells, as well as tetracycline or ampicillin resistance gene for *E. coli*.

The vector containing said DNA sequence and proper promoter or regulatory elements can be transformed into appropriate host cells to express the protein.

The "host cell" includes prokaryote, e.g., bacteria; primary eukaryote, e.g., yeast; advanced eukaryotic, e.g., mammalian cells. The representative examples are bacterial cells, e.g., *E. coli, Streptomyces, Salmonella typhimurium*; fungal cells, e.g., yeast; plant cells; insect cells e.g., *Drosophila* S2 or Sf9; animal cells e.g., CHO, COS, 293 cells or Bowes melanoma, etc.

Transcription of the polynucleotide in higher eukaryotes is increased by inserting an enhancer sequence into the vector. Enhancers are cis-acting elements of DNA, usually about 10-300 bps, that act on a promoter to increase gene transcription. Examples include SV40 enhancer on the late side of replication origin 100 to 270 bp, the polyoma enhancer on the late side of replication origin, and adenovirus enhancers.

The artisans know clearly how to select appropriate vectors, promoters, enhancers and host cells.

Recombinant transformation of host cell with the DNA might be carried out by conventional techniques known to the artisans. Where the host is prokaryotic, e.g., *E. coli*, the competent cells capable of DNA uptake, can be prepared from cells harvested after exponential growth phase and subsequently treated by the $CaCl_2$ method using known procedures. Alternatively, $MgCl_2$ can be used. The transformation can also be carried out by electroporation. When the host is an eukaryote, transfection of DNA such as calcium phosphate co-precipitates, conventional mechanical procedures e.g., micro-injection, electroporation, or liposome-mediated transfection may be used.

The transformants are cultured conventionally to express Rhor polypeptide of invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out. If desired, the physical, chemical and other properties can be utilized in various isolation methods to isolate and purify the recombinant protein. These methods are well-known to the artisans and include, but are not limited to conventional renaturation treatment, treatment by protein precipitant (e.g., salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and the combination thereof.

Therefore, the recombinant human Rhor protein or polypeptide have various uses including, but not to be limited to: curing disorders caused by low or no activity of Rhor protein (e.g., baldness), and screening out antibodies, polypeptides or ligands as agonists or antagonists of Rhor. For example, antibodies can be used to activate or inhibit the function of Rhor protein. The expressed recombinant Rhor protein can be used to screen polypeptide library to find out therapeutically valuable polypeptide molecules which inhibit or activate Rhor protein.

In another aspect, the invention also includes polyclonal and monoclonal antibodies (mAbs), preferably mAbs, which are specific for polypeptides encoded by Rhor DNA or fragments thereof. By "specificity", it means an antibody which binds to the Rhor gene products or a fragments thereof. Preferably, the antibody binds to the Rhor gene products or fragments thereof and does not substantially recognize nor bind to other antigenically unrelated molecules. Antibodies which bind to Rhor and block Rhor protein and those which do not affect the Rhor function are included in the invention.

The invention includes intact monoclonal or polyclonal antibodies, and immunologically-active antibody fragments, e.g., a Fab' or $(Fab)_2$ fragment, an antibody heavy chain, an antibody light chain, or a chimeric antibody.

The antibodies in the present invention can be prepared by various techniques known in the art. E.g., purified Rhor gene products, or its antigenic fragments can be administered to animals (e.g., rabbit, mice and rat) to produce polyclonal antibodies. Similarly, cells expressing Rhor or its antigenic fragments can be used to immunize animals to produce antibodies. The antibody of the invention can be monoclonal antibodies (mAbs). The mAbs can be prepared using hybridoma technique. Antibodies comprise those which block Rhor function and those which do not affect Rhor function. Antibodies can be produced by routine immunology techniques and using fragments or functional regions of Rhor gene product prepared by recombinant methods or synthesized by a polypeptide synthesizer. The antibodies binding to unmodified Rhor gene product can be produced by immunizing animals with gene products produced by prokaryotic cells (e.g., *E. coli*), and the antibodies binding to post-translationally modified forms thereof can be acquired by immunizing animals with gene products produced by eukaryotic cells (e.g., yeast or insect cells).

The antibody against Rhor can be used in immunohistochemical method to detect the presence of Rhor protein in biopsy specimen. The mAb can be radiolabelled and injected into body to trace the position and distribution of Rhor.

The polyclonal antibodies can be prepared by immunizing animals, such as rabbit, mouse, and rat, with Rhor protein. Various adjuvants, e.g., Freund's adjuvant, can be used to enhance the immunization.

The substances which act with Rhor protein, e.g., receptors, inhibitors, agonists and antagonists, can be screened out by various conventional techniques, using Rhor protein.

The Rhor protein, antibody, inhibitor, agonist or antagonist of the invention provide different effects when administered in therapy. Usually, these substances are formulated with a non-toxic, inert and pharmaceutically acceptable aqueous carrier. The pH typically is about 5-8, preferably 6-8, although pH may alter according to the property of the formulated substances and the diseases to be treated. The formulated pharmaceutical composition is administered in conventional routes including, but not limited to, oral, intramuscular, intraperitoneal, intravenous, subcutaneous, intradermal or topical administration.

The Rhor polypeptide can be directly used for curing disorders, e.g., baldness. The Rhor protein can be administrated in combination with other medicaments used for treating baldness.

The invention also provides a pharmaceutical composition comprising safe and effective amount of Rhor protein or its agonist or antagonist in combination with a pharmaceutically acceptable carrier. Such a carrier includes but is not limited to saline, buffer solution, glucose, water, glycerin, ethanol, or the combination thereof. The pharmaceutical formulation should be suitable for delivery method. The pharmaceutical composition may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administered in therapeutically effective amount, e.g., about 1 ug-5 mg/kg body weight per day. Moreover, the polypeptide of invention can be administrated together with other therapeutic agents.

When using pharmaceutical composition, the safe and effective amount of the Rhor protein or its antagonist or agonist is administrated to mammals. Typically, the safe and effective amount is at least about 10 ug/kg body weight and less than about 5 mg/kg body weight in most cases, and preferably about 10 ug-1 mg/kg body weight. Certainly, the precise amount depends upon various factors, such as delivery methods, the subject health, etc., and is within the judgment of the skilled clinician.

Rhor polynucleotides also have many therapeutic applications. Gene therapy technology can be used in the therapy of baldness, which is caused by the loss of Rhor expression or the expression of abnormal or non-active Rhor. The expression vectors derived from virus, such as retrovirus, adenovirus, adeno-associated virus, herpes simplex virus, parvovirus, and so on, can be used to introduce the Rhor gene into the cells. In addition, the recombinant Rhor gene can be packed into liposome and then transferred into the cells.

The methods for introducing the polynucleotides into tissues or cells include: directly injecting the polynucleotides into tissue in the body, in vitro introducing the polynucleotides into cells with vectors, such as virus, phage, or plasmid, and then transplanting the cells into the body.

The polypeptide molecule capable of binding Rhor protein can be obtained by screening out the random polypeptide library consisting of the various combinations of amino acids bound onto the solid matrix. In the screening procedure, Rhor protein should be labeled.

The invention further provides diagnostic assays for quantitative and in situ measurement of Rhor protein level. These assays are known in the art and include FISH assay and radioimmunoassay. The level of Rhor protein detected in the assay can be used to illustrate the importance of Rhor protein in diseases and to determine the Rhor-related diseases such as baldness.

A method of detecting Rhor protein in a sample by utilizing the antibody specifically against Rhor protein comprises the steps of: contacting the sample with the antibody specifically against Rhor protein; observing the formation of antibody complex which indicates the presence of Rhor protein in the sample.

The polynucleotide encoding Rhor protein can be used in the diagnosis and treatment of Rhor related diseases. In diagnosis, the polynucleotide encoding Rhor can be used to detect whether Rhor is expressed or not, and whether the expression is normal or abnormal in the case of diseases. Rhor DNA sequences can be used in the hybridization with biopsy samples to determine Rhor expression. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analyzing the differential expression of genes in tissues and for the diagnosis of genes. The Rhor specific primers can be used in RT-PCR and in vitro amplification to detect the transcripts of Rhor.

Detection of Rhor gene mutation is useful for the diagnosis of Rhor related diseases. The mutation forms of Rhor include site mutation, translocation, deletion, rearrangement and any other mutations compared with the wild-type Rhor DNA sequence. The conventional methods, e.g., Southern blotting, DNA sequencing, PCR and in situ blotting, can be used to detect mutation. Moreover, mutation sometimes affects protein expression. Therefore, Northern blotting and Western blotting can be used to indirectly determine the gene mutation. The experiments of the invention has indicated that the mutation of Rhor is directly related to baldness.

In one embodiment of the invention, a new gene was determined based on the phenotype and genetic analysis on the mice without hair, mice with little hair and mice with normal hair. The corresponding polynucleotide sequence was isolated. It encoded a polypeptide having the amino acid sequence shown in SEQ ID NO: 2. The polynucleotide of the invention was shown in SEQ ID NO: 1. The full-length sequence comprises 2484 bps, while the ORF is nucleotides 1-2481 and encodes a Rhor protein having 827 amino acids (SEQ ID NO: 2). The studies showed that the mutation of the gene results in the blocking of signaling, thereby influencing the development of follicular cells and causing the congenital baldness in mice. Because of the high homology in the encoding region of Rhor protein, the partial deletion of the corresponding human gene in the genome is likely to cause the congenital baldness or little hair.

The Rhor provides new approach for curing diseases such as baldness, thus having huge potential applications.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Mapping the Baldness Related Gene

A hairless mutation was found in wildtype Balb/c, heterozygous was sparse hair, while homozygote was hairless. All the descendants of homozygote and wild type mice showed sparse hair phenotype. Inbred of heterozygous showed segregation of character and the ratio of phenotype of wildtype:sparse hair:hairless was 1:2:1 represented by Mendel's relativity of segregation. Further, according to the pedigree analysis, this mutation was a single gene incomplete dominance.

Genomic DNA of 2000 mice was extracted for genotyping, and the data were analyzed by computer using the software Linkage. The mutation was mapped to a region between two microsatellite marker D11mit103 and D11mit338, and the mapping range was 1,700 kb. The precision map was then generated to narrowing the mutation to a region of 800 kb.

Scaning the genome was carried out by sequencing the whole region, thereby mapping the mutation to a narrow region.

EXAMPLE 2

Genomic DNA Deletion Assay

According to the standard method described in Molecular Cloning, the genomic DNA was extracted from hairless, sparse hair and wildtype mice tissue. The following primers were used.

```
                                              (SEQ ID NO:3)
Forward primer: 5' gcaggctagcgtgttaaagg 3'

(SEQ ID NO:4)
Reverse primer: 5' aaaacggggtcatagcagc 3'
```

The mice DNA was used as templates to perform polymerase chain reaction with the Taq Gold polymerase commercial available from Applied Bio-system under the following thermal conditions:

| Hot start of Taq polymerase and template denaturing: | |
| --- | --- |
| 95° C. | 10 min |
| first round of thermal cycle: | |
| 95° C. | 30 sec |
| 68° C. | 45 sec |
| perform 1° C. decrease per cycle | |
| 72° C. | 2 min 30 sec |
| repeat 12 times | |
| second round of thermal cycle: | |
| 95° C. | 30 sec |
| 56° C. | 45 sec |
| 72° C. | 2 min 30 sec |
| repeat 35 times | |
| 72° C. | 10 min |

Figure 1:
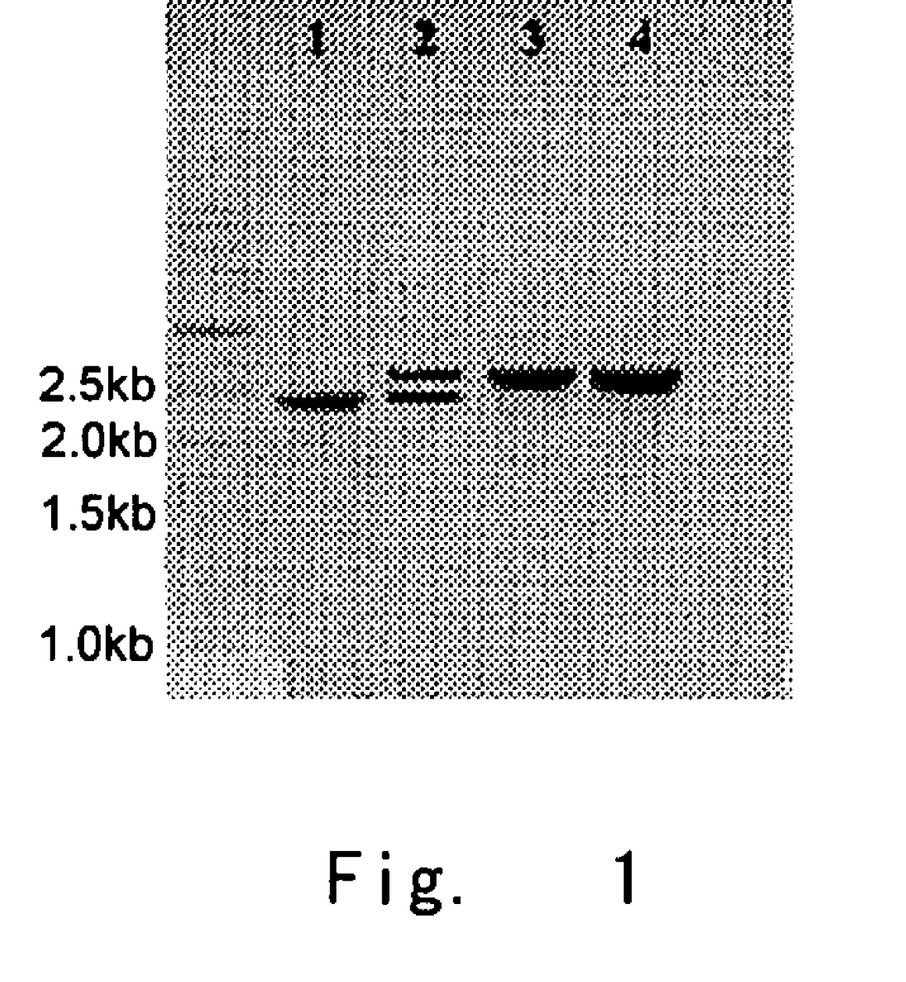
FIG. 1 shows the PCR amplification results of Rhor gene in different mice. Lane 1: mice without hair; Lane 2: mice with little hair; Lane 3 and 4: normal mice.

The PCR product was analyzed on a 1.0% agarose gel followed by ethidium bromide staining (FIG. 1). Product of heterozygous showed two bands, matching the bands from wildtype mice and homozygote hairless mice.

EXAMPLE 3

Rhor Gene Genomic Sequencing

In this Example, the genomic sequencing was performed to confirm the correlation between Rhor and hairless phenotype.

The PCR product in Example 2 was purified by Omega Cycle-Pure Kit. The following primers were used.

```
                                              (SEQ ID NO: 5)
Forward primer: 5' gcacatctgagggaaggaag 3'

(SEQ ID NO: 6)
Reverse primer: 5' cttccggtcaaatgcaaagt 3'
```

The sequence was performed on the 3100 automatic sequencer, using BigDye terminal reagent purchased from Applied Biosystem and the following thermal conditions:

| Template denature | |
| --- | --- |
| 98° C. | 2 min |
| 96° C. | 20 sec |
| 51° C. | 20 sec |
| 60° C. | 4 min |
| repeat 25 times | |

Result of sequencing:

```
                                                              (SEQ ID NO: 7)
AGCCTACCTG AAGAGTGTCA GCCTACAGGA GCCCCGGGGA CGATGGCAGG AGGGCGCAGA    60

GAAGCGCCCC GGCTTCCGCC GCCAGGCCTC CCTGTCCCAG AGCATCCGCA AGAGCACAGC   120

CCAGTGGTTT GGGGTCAGCG GCGACTGGGA GGGCAAGCGA CAAAACTGGC ATCGTCGCAG   180

CCTGCACCAC TGCAGCGTGC ACTATGGCCG CCTCAAGGCC TCGTGCCAGA GAGAACTGGA   240

CCTGCCCAGC CAGGAGGTGC CATCCTTCCA GGGCACTGAG TGTCCAAAAC CGTGCAAGAT   300

GCCCAAGATT GTGGATCCAC TGGCTCGGGG TAGGGCGTTC CGCCATCCAG ATGAGGTGGA   360

CCGGCCTCAC GCTGCCCACC CACCTCTGAC TCCAGGGGTC CTGTCTCTCA CATCCTTCAC   420

CATGTCCGCT CTGGCTACTC CCATCTGCCC CGCCGCAAGA GGATATCTGT TGCCCATATG   480

AGCTTTCAGG CAGCCGCCGC CCTCCTCAAG GGGCGTTCCG TGCTAGATGC GACTGGGCAG   540

CGGTGGCGGC ATGTCAAACG CAGCTTCGCT TACCCCAGGT TCCTGGAGGA GGATGCTGTC   600
```

Comparing the sequence of wildtype mice with that of homozygote hairless mice, it could be seen that there was a 230 bp deletion in the genome sequence of hairless mice (underlined portion).

EXAMPLE 4

Obtain the Complete ORF of Rhor

Using Total RNA extract kit from Qiagen, the mice skin total RNA was extracted and the RNA was analyzed on a 1% agarose gel and converted to cDNA by reverse transcription using Reverse Transcription System from Promega.

The following primers was used in PCR reaction:

```
                                              (SEQ ID NO: 8)
Forward primer: 5' ACTCTGCTCTCAGCCGCTT 3'

(SEQ ID NO: 9)
Reverse primer: 5' CCAGACACATGCTGGAGCTA 3'
```

Polymerase: Takara LA polymerase
PCR thermal condition:

| | |
|---|---|
| 95° C. | 30 sec |
| 54° C. | 45 sec |
| 72° C. | 3 min |
| repeat 45 times | |
| 72° C. | 10 min |

The product was separated on a 0.8% agarose electrophoresis. The gel was cut and purified, thereby obtaining the target band from gel. The full length ORF of Rhor was obtained by sequencing.

The Rhor full length ORF was shown in SEQ ID NO:1 and the encoded amino acid sequence was shown in SEQ ID NO:2.

EXAMPLE 5

Rhor cDNA Deletion Assay

The cDNA from Example 4 was used as template and the PCR reaction was performed using Taq Gold polymerase and the following primers:

```
                                              (SEQ ID NO: 10)
Forward primer: 5' gcacatctgagggaaggaag 3'

(SEQ ID NO: 11)
Reverse primer: 5' cttccggtcaaatgcaaagt 3'
```

PCR thermal condition:

| Hot start of Taq polymerase and template denaturing: | |
|---|---|
| 95° C. | 10 min |
| First round of thermal cycle | |
| 95° C. | 30 sec |
| 68° C. | 45 sec |
| perform 1° C. decrease per cycle | |
| 72° C. | 90 sec |
| repeat 14 times | |
| second round of thermal cycle | |
| 95° C. | 30 sec |
| 54° C. | 45 sec |
| 72° C. | 90 sec |
| repeat 40 times | |
| 72° C. | 10 min |

The products were analyzed on a 0.8% agarose gel and purified using Cycle-Pure Kit from Omega. The sequencing reaction was carried out using the same primer and BigDye terminal reagent from Applied Biosystem

| template denature | |
|---|---|
| 98° C. | 2 min |
| 96° C. | 20 sec |
| 51° C. | 20 sec |
| 60° C. | 4 min |
| repeat 25 times | |

Results:

```
                                                                (SEQ ID NO: 12)
GTGTCAGCCT ACAGGAGCCC CGGGGACGAT GGCAGGAGGG CGCAGAGAAG CGCCCCGGCT   60

TCCGCCGCCA GGCCTCCCTG TCCCAGAGCA TCCGCAAGAG CACAGCCCAG TGGTTTGGGG  120

TCAGCGGCGA CTGGGAGGGC AAGCGACAAA ACTGGCATCG TCGCAGCCTG CACCACTGCA  180

GCGTGCACTA TGGCCGCCTC AAGGCCTCGT GCCAGAGAGA ACTGGAGCTG GCCAGCCAGG  240

AGGTGCCATC CTTCCAGGGC ACTGAGTCTC CAAAACCGTG CAAGATGCCC AAGATTGTGG  300

ATCCACTGGC TCGGGGTAGG GCCTTCCGCG ATGCAGATGA CGTGGACCGO CCTCACGCTG  360

CCCACCCACC TCTGACTCCA GGGGTCCTGT CTCTCACATC CTTCACCATG TCCGCTCTGG  420

CTACTCCCAT CTGCCCCGCC GCAAGAGGAT ATCTGTTGCC CATATGAGCT TTCAGGCAGC  480

CGCCGCCCTC CTCAAGGGGC GTTCCGTGCT AGATGCGACT GGGCAGCGGT GCCGGCATGT  540

CAAACGCAGC TTCGCTTACC CCAGCTTCCT GGAGGAGGAT GCTGTCGATG GAGCTGACAC  600
```

The underlined sequence showed the cDNA deletion in homozygote hairless mice, which was the same as that deletion in genomic sequence.

EXAMPLE 6

Rhor Coding Protein Structure Analyze

Structure analysis showed the encoded protein of Rhor contained two highly conserved domains:

(1) The amino acids 619-759 in Rhor encoded protein formed a Rhomboid domain, suggesting that Rhor protein was a Rhomboid protein family member. The members of this family were found in bacteria and eukaryotes and most of them were membrane proteins. These proteins contained three highly conserved histidines in the putative transmembrane regions that might be involved in the peptidase function.

(2) The amino acids 610-804 in Rhor encoded protein formed a competence structure domain, suggesting Rhor protein was a member of the competence protein family. Most of the member in this family were membrane proteins. They had six helix trans-membrane structures. These protein transported nucleic acid through the membrane. Some of the family members were reported as critical elements when bacterium intakes extracellular DNA. All family members had an amino-terminal trans-membrane region, and two histidines in this region formed a highly conserved motif as the binding site for metal ion.

The above structural analysis showed that the mutated Rhor protein might be functionally defective in transporting message RNA, thereby blocking the hair-follicle development.

EXAMPLE 7

Multiple Functions of Rhor

Homozygote hairless mice were leaner than wild type mice. The axungia reservation was seldom found in dissection, suggesting that Rhor might also participate in axungia metabolism and the mutation would cause axungia metabolic disorder.

Further, the lymphadenoma was found during the hairless mice life span and lymphocyte lost its normal growing regulation. This suggested that Rhor could be in the regulation point of multiple pathways.

EXAMPLE 8

Rhor Expression in Prokaryocyte

The following primers was synthesized:

forward primers 5'C GGATCCATGGCCTCAGCTGACAAGAATGGCAG CAACCTCCCA 3(SEQ ID NO:13) (BamHI recognition site GGATCC was introduced and the first C was protective base)

reverse primer: 5'ATA AAGCTTGCTCGATCTGGTCCACGATGTGATT 3(SEQ ID NO:14) (HindIII recognition site AAGCTT was introduced and ATA were protective bases)

The mice cDNA was used as template in the amplification of DNA encoding Rhor protein.

BamHI and Hind III recognition sites were used to clone the PCR product into expression vector pET32a(Novagen) digested with the same enzymes. The vector was transformed into host *E. Coli*:BL21(DE3). Transformed host expressed the foreign protein when induced by IPTG.

The expressed protein had a molecular weight of about 90 Kda in SDS-PAGE.

EXAMPLE 9

Antibody Preparation

The protein obtained in Example 8 was used as an antigen to prepare polyclonal antibody in rabbits. The procedure was as follows: The rabbits were immunized with 240 ug protein per rabbit in complete Freund's adjuvant. The rabbits were immunized again after four weeks with 140 ug protein per rabbit in incomplete Freund's adjuvant. Finally, the rabbits were immunized two weeks later with 120 ug protein per rabbit in incomplete Freund's adjuvant.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

---

What is claimed is:

1. An isolated polynucleotide comprising a nucleotide sequence selected from the group consisting of:
   (a) the nucleotide sequence encoding the polypeptide comprising the amino acid sequence of SEQ ID NO: 2;
   (b) the polynucleotide fully complementary to nucleotide sequence of (a).

2. The polynucleotide of claim 1 wherein said nucleotide sequence encodes a polypeptide having the amino acid sequence of SEQ ID NO: 2.

3. The polynucleotide of claim 1 wherein said nucleotide sequence comprises nucleotides 1-2484 of the nucleotide sequence of SEQ ID NO: 1.

4. A vector containing the polynucleotide of claim 1.

5. An isolated genetically engineered host cell containing the vector of claim 4.

6. A method for producing Rhor protein comprising the following steps:
   (a) culturing the host cell of claim 5 under the conditions suitable for expression of protein;
   (b) isolating the Rhor protein from the culture.

7. An isolated Rhor polypeptide comprising the amino acid sequence of SEQ ID NO: 2.

8. The polypeptide of claim 7 wherein the polypeptide is a polypeptide having the amino acid sequence of SEQ ID NO: 2.

* * * * *

SEQUENCE LISTING

```
<160> NUMBER OF SEQ ID NOS: 14

<210> SEQ ID NO 1
<211> LENGTH: 2484
<212> TYPE: DNA
<213> ORGANISM: Mus musculus
<220> FEATURE:
<221> NAME/KEY: CDS
<222> LOCATION: (1)..(2481)
<223> OTHER INFORMATION:

<400> SEQUENCE: 1 atg gcc tca gct gac aag aat ggc agc aac ctc cca tct gtg tct ggt      48
Met Ala Ser Ala Asp Lys Asn Gly Ser Asn Leu Pro Ser Val Ser Gly
1               5                   10                  15 agc cgc ctg cag agc cgg aag cca ccc aac ctc tcc atc acc atc ccg      96
Ser Arg Leu Gln Ser Arg Lys Pro Pro Asn Leu Ser Ile Thr Ile Pro
            20                  25                  30
```

-continued

| | | |
|---|---|---|
| cca cca gag agc cag gcc ccc ggc gag cag gat agc atg ctt cct gag<br>Pro Pro Glu Ser Gln Ala Pro Gly Glu Gln Asp Ser Met Leu Pro Glu<br>35                          40                          45 | 144 | |
| agg cgc aag aac cca gcc tac ctg aag agt gtc agc cta cag gag ccc<br>Arg Arg Lys Asn Pro Ala Tyr Leu Lys Ser Val Ser Leu Gln Glu Pro<br>50                          55                          60 | 192 | |
| cgg gga cga tgg cag gag ggc gca gag aag cgc ccc ggc ttc cgc cgc<br>Arg Gly Arg Trp Gln Glu Gly Ala Glu Lys Arg Pro Gly Phe Arg Arg<br>65                          70                          75                          80 | 240 | |
| cag gcc tcc ctg tcc cag agc atc cgc aag agc aca gcc cag tgg ttt<br>Gln Ala Ser Leu Ser Gln Ser Ile Arg Lys Ser Thr Ala Gln Trp Phe<br>                85                          90                          95 | 288 | |
| ggg gtc agc ggc gac tgg gag ggc aag cga caa aac tgg cat cgt cgc<br>Gly Val Ser Gly Asp Trp Glu Gly Lys Arg Gln Asn Trp His Arg Arg<br>              100                     105                     110 | 336 | |
| agc ctg cac cac tgc agc gtg cac tat ggc cgc ctc aag gcc tcg tgc<br>Ser Leu His His Cys Ser Val His Tyr Gly Arg Leu Lys Ala Ser Cys<br>              115                     120                     125 | 384 | |
| cag aga gaa ctg gag ctg ccc agc cag gag gtg cca tcc ttc cag ggc<br>Gln Arg Glu Leu Glu Leu Pro Ser Gln Glu Val Pro Ser Phe Gln Gly<br>130                        135                        140 | 432 | |
| act gag tct cca aaa ccg tgc aag atg ccc aag att gtg gat cca ctg<br>Thr Glu Ser Pro Lys Pro Cys Lys Met Pro Lys Ile Val Asp Pro Leu<br>145                        150                        155                  160 | 480 | |
| gct cgg ggt agg gcc ttc cgc cat cca gat gag gtg gac cgg cct cac<br>Ala Arg Gly Arg Ala Phe Arg His Pro Asp Glu Val Asp Arg Pro His<br>                       165                     170                     175 | 528 | |
| gct gcc cac cca cct ctg act cca ggg gtc ctg tct ctc aca tcc ttc<br>Ala Ala His Pro Pro Leu Thr Pro Gly Val Leu Ser Leu Thr Ser Phe<br>              180                     185                     190 | 576 | |
| acc agt gtc cgc tct ggc tac tcc cat ctg ccc cgc cgc aag agg ata<br>Thr Ser Val Arg Ser Gly Tyr Ser His Leu Pro Arg Arg Lys Arg Ile<br>              195                     200                     205 | 624 | |
| tct gtt gcc cat atg agc ttt cag gca gcc gcc ctc ctc aag ggg<br>Ser Val Ala His Met Ser Phe Gln Ala Ala Ala Leu Leu Lys Gly<br>210                        215                        220 | 672 | |
| cgt tcc gtg cta gat gcg act ggg cag cgg tgc cgg cat gtc aaa cgc<br>Arg Ser Val Leu Asp Ala Thr Gly Gln Arg Cys Arg His Val Lys Arg<br>225                        230                        235                  240 | 720 | |
| agc ttc gct tac ccc agc ttc ctg gag gag gat gct gtc gat gga gct<br>Ser Phe Ala Tyr Pro Ser Phe Leu Glu Glu Asp Ala Val Asp Gly Ala<br>                       245                     250                     255 | 768 | |
| gac acc ttc gac tcc tcc ttt ttt agt aag gaa gaa atg agc tcc atg<br>Asp Thr Phe Asp Ser Ser Phe Phe Ser Lys Glu Glu Met Ser Ser Met<br>                       260                     265                     270 | 816 | |
| cct gac gat gtc ttt gag tcc ccc cca ctc tct gcc agc tac ttc cga<br>Pro Asp Asp Val Phe Glu Ser Pro Pro Leu Ser Ala Ser Tyr Phe Arg<br>                      275                     280                     285 | 864 | |
| ggt gtc cca cac tct gcc tcc ccg gtc tcc ccg gat gga gtg cac atc<br>Gly Val Pro His Ser Ala Ser Pro Val Ser Pro Asp Gly Val His Ile<br>              290                     295                     300 | 912 | |
| ccg cta aaa gaa tac agc ggt ggc cga gcc ctg ggt ccc ggg acc cag<br>Pro Leu Lys Glu Tyr Ser Gly Gly Arg Ala Leu Gly Pro Gly Thr Gln<br>305                        310                        315                  320 | 960 | |
| cgt ggc aaa cgc att gcc tcc aaa gta aag cac ttt gca ttt gac cgg<br>Arg Gly Lys Arg Ile Ala Ser Lys Val Lys His Phe Ala Phe Asp Arg<br>                       325                     330                     335 | 1008 | |
| aag aag agg cac tac ggc ctg ggt gtc gtg ggt aac tgg ctc aac cga<br>Lys Lys Arg His Tyr Gly Leu Gly Val Val Gly Asn Trp Leu Asn Arg | 1056 | |

-continued

```
                    340                     345                     350
agc tat cga cgc agc atc agc agc acc gtg cag cgg cag ctg gag agc         1104
Ser Tyr Arg Arg Ser Ile Ser Ser Thr Val Gln Arg Gln Leu Glu Ser
        355                     360                     365 ttc gat agc cac cgg ccc tac ttc acc tac tgg ctg acg ttc gtt cac         1152
Phe Asp Ser His Arg Pro Tyr Phe Thr Tyr Trp Leu Thr Phe Val His
    370                     375                     380 atc atc atc acc ttg ctg gtg atc tgc acc tat ggc atc gca cct gtg         1200
Ile Ile Ile Thr Leu Leu Val Ile Cys Thr Tyr Gly Ile Ala Pro Val
385                     390                     395                 400 ggc ttt gcc cag cac gtt acc acc cag ctg gtg ctg aag aac aga ggc         1248
Gly Phe Ala Gln His Val Thr Thr Gln Leu Val Leu Lys Asn Arg Gly
                405                     410                     415 gtg tat gag agc gtg aag tac atc cag cag gag aac ttc tgg att ggc         1296
Val Tyr Glu Ser Val Lys Tyr Ile Gln Gln Glu Asn Phe Trp Ile Gly
            420                     425                     430 ccc agc tcg att gac ctc atc cac ctg gga gca aag ttc tcg ccc tgc         1344
Pro Ser Ser Ile Asp Leu Ile His Leu Gly Ala Lys Phe Ser Pro Cys
        435                     440                     445 atc cgg aag gac cag caa att gag cag ctg gta cgg agg gag cgc gac         1392
Ile Arg Lys Asp Gln Gln Ile Glu Gln Leu Val Arg Arg Glu Arg Asp
    450                     455                     460 att gag cgc acc tct ggc tgc tgt gtc cag aat gac cgc tcg ggc tgc         1440
Ile Glu Arg Thr Ser Gly Cys Cys Val Gln Asn Asp Arg Ser Gly Cys
465                     470                     475                 480 atc cag acc ctg aag aag gac tgc tcg gag act tta gcc acg ttc gta         1488
Ile Gln Thr Leu Lys Lys Asp Cys Ser Glu Thr Leu Ala Thr Phe Val
                485                     490                     495 aag tgg cag aat gat act ggg ccc tca gac aag tct gac ctg agc cag         1536
Lys Trp Gln Asn Asp Thr Gly Pro Ser Asp Lys Ser Asp Leu Ser Gln
            500                     505                     510 aag cag cca tcg gcg gtt gtg tgc cac caa gac ccc agg acc tgt gaa         1584
Lys Gln Pro Ser Ala Val Val Cys His Gln Asp Pro Arg Thr Cys Glu
        515                     520                     525 gag cct gcc tcc agt ggg gcc cac atc tgg cct gat gac att acc aag         1632
Glu Pro Ala Ser Ser Gly Ala His Ile Trp Pro Asp Asp Ile Thr Lys
    530                     535                     540 tgg ccg atc tgc aca gag cag gct cag agc aac cac acg ggc ttg ttg         1680
Trp Pro Ile Cys Thr Glu Gln Ala Gln Ser Asn His Thr Gly Leu Leu
545                     550                     555                 560 cac ata gac tgt aag atc aaa ggc cgc ccc tgc tgc atc ggc acc aag         1728
His Ile Asp Cys Lys Ile Lys Gly Arg Pro Cys Cys Ile Gly Thr Lys
                565                     570                     575 ggc agc tgc gag atc acc act cgg gag tac tgt gag ttc atg cat ggc         1776
Gly Ser Cys Glu Ile Thr Thr Arg Glu Tyr Cys Glu Phe Met His Gly
            580                     585                     590 tat ttc cat gaa gac gcg acg ctg tgt tcc cag gtg cac tgt tta gac         1824
Tyr Phe His Glu Asp Ala Thr Leu Cys Ser Gln Val His Cys Leu Asp
        595                     600                     605 aag gtg tgt ggg ctc ctg cct ttc ctc aac cct gag gtc cct gac cag         1872
Lys Val Cys Gly Leu Leu Pro Phe Leu Asn Pro Glu Val Pro Asp Gln
    610                     615                     620 ttc tac cgg atc tgg ctg tct tta ttc ctg cat gct ggc ata gtg cac         1920
Phe Tyr Arg Ile Trp Leu Ser Leu Phe Leu His Ala Gly Ile Val His
625                     630                     635                 640 tgc ctt gtg tct gtg gtc ttc caa atg acc atc ctg agg gac cta gag         1968
Cys Leu Val Ser Val Val Phe Gln Met Thr Ile Leu Arg Asp Leu Glu
                645                     650                     655 aag ctg gcc ggc tgg cac cgc atc tcc atc atc ttc atc ctt agt ggc         2016
```

```
Lys Leu Ala Gly Trp His Arg Ile Ser Ile Ile Phe Ile Leu Ser Gly
                660                 665                 670 att aca ggc aac ctg gcc agc gcc atc ttc ctc ccc tac cgg gca gag    2064
Ile Thr Gly Asn Leu Ala Ser Ala Ile Phe Leu Pro Tyr Arg Ala Glu
            675                 680                 685 gtg ggc cca gcc ggg tcg cag ttc ggc ctc ctc gcc tgc ctc ttc gtg    2112
Val Gly Pro Ala Gly Ser Gln Phe Gly Leu Leu Ala Cys Leu Phe Val
        690                 695                 700 gag ctg ttc cag agc tgg cag ctg ttg gag cgg ccg tgg aag gcc ttc    2160
Glu Leu Phe Gln Ser Trp Gln Leu Leu Glu Arg Pro Trp Lys Ala Phe
705                 710                 715                 720 ttc aac ctg tcg gcc att gtg ctt ttc ctc ttc atc tgt ggc ctc ctg    2208
Phe Asn Leu Ser Ala Ile Val Leu Phe Leu Phe Ile Cys Gly Leu Leu
                725                 730                 735 ccc tgg ata gac aac atc gcc cac atc ttc ggg ttc ctc agc ggc atg    2256
Pro Trp Ile Asp Asn Ile Ala His Ile Phe Gly Phe Leu Ser Gly Met
            740                 745                 750 ctt ctg gcc ttc gcc ttc ctg cct tac att acc ttc ggc acc agc gac    2304
Leu Leu Ala Phe Ala Phe Leu Pro Tyr Ile Thr Phe Gly Thr Ser Asp
        755                 760                 765 aag tac cgc aag cga gcc ctc atc ctc gtg tcg ctg ctg gtc ttt gct    2352
Lys Tyr Arg Lys Arg Ala Leu Ile Leu Val Ser Leu Leu Val Phe Ala
770                 775                 780 ggg ctc ttt gct tcc ctg gtg ctg tgg ctg tac atc tac ccc atc aac    2400
Gly Leu Phe Ala Ser Leu Val Leu Trp Leu Tyr Ile Tyr Pro Ile Asn
785                 790                 795                 800 tgg ccc tgg atc gag tac ctc acc tgc ttt ccc ttc acc agc cgc ttc    2448
Trp Pro Trp Ile Glu Tyr Leu Thr Cys Phe Pro Phe Thr Ser Arg Phe
                805                 810                 815 tgt gag aag tac gag cta gac cag gtg cta cac taa                    2484
Cys Glu Lys Tyr Glu Leu Asp Gln Val Leu His
            820                 825

<210> SEQ ID NO 2
<211> LENGTH: 827
<212> TYPE: PRT
<213> ORGANISM: Mus musculus

<400> SEQUENCE: 2

Met Ala Ser Ala Asp Lys Asn Gly Ser Asn Leu Pro Ser Val Ser Gly
1               5                   10                  15

Ser Arg Leu Gln Ser Arg Lys Pro Pro Asn Leu Ser Ile Thr Ile Pro
            20                  25                  30

Pro Pro Glu Ser Gln Ala Pro Gly Glu Gln Asp Ser Met Leu Pro Glu
        35                  40                  45

Arg Arg Lys Asn Pro Ala Tyr Leu Lys Ser Val Ser Leu Gln Glu Pro
    50                  55                  60

Arg Gly Arg Trp Gln Glu Gly Ala Glu Lys Arg Pro Gly Phe Arg Arg
65                  70                  75                  80

Gln Ala Ser Leu Ser Gln Ser Ile Arg Lys Ser Thr Ala Gln Trp Phe
                85                  90                  95

Gly Val Ser Gly Asp Trp Glu Gly Lys Arg Gln Asn Trp His Arg Arg
            100                 105                 110

Ser Leu His His Cys Ser Val His Tyr Gly Arg Leu Lys Ala Ser Cys
        115                 120                 125

Gln Arg Glu Leu Glu Leu Pro Ser Gln Glu Val Pro Ser Phe Gln Gly
    130                 135                 140

Thr Glu Ser Pro Lys Pro Cys Lys Met Pro Lys Ile Val Asp Pro Leu
```

```
                    145                 150                 155                 160
            Ala Arg Gly Arg Ala Phe Arg His Pro Asp Glu Val Asp Arg Pro His
                            165                 170                 175

Ala Ala His Pro Pro Leu Thr Pro Gly Val Leu Ser Leu Thr Ser Phe
                        180                 185                 190

Thr Ser Val Arg Ser Gly Tyr Ser His Leu Pro Arg Arg Lys Arg Ile
                        195                 200                 205

Ser Val Ala His Met Ser Phe Gln Ala Ala Ala Leu Leu Lys Gly
                    210                 215                 220

Arg Ser Val Leu Asp Ala Thr Gly Gln Arg Cys Arg His Val Lys Arg
            225                 230                 235                 240

Ser Phe Ala Tyr Pro Ser Phe Leu Glu Glu Asp Ala Val Asp Gly Ala
                            245                 250                 255

Asp Thr Phe Asp Ser Ser Phe Phe Ser Lys Glu Glu Met Ser Ser Met
                        260                 265                 270

Pro Asp Asp Val Phe Glu Ser Pro Leu Ser Ala Ser Tyr Phe Arg
                        275                 280                 285

Gly Val Pro His Ser Ala Ser Pro Val Ser Pro Asp Gly Val His Ile
                    290                 295                 300

Pro Leu Lys Glu Tyr Ser Gly Gly Arg Ala Leu Gly Pro Gly Thr Gln
            305                 310                 315                 320

Arg Gly Lys Arg Ile Ala Ser Lys Val Lys His Phe Ala Phe Asp Arg
                            325                 330                 335

Lys Lys Arg His Tyr Gly Leu Gly Val Val Gly Asn Trp Leu Asn Arg
                        340                 345                 350

Ser Tyr Arg Arg Ser Ile Ser Ser Thr Val Gln Arg Gln Leu Glu Ser
                        355                 360                 365

Phe Asp Ser His Arg Pro Tyr Phe Thr Tyr Trp Leu Thr Phe Val His
                    370                 375                 380

Ile Ile Ile Thr Leu Leu Val Ile Cys Thr Tyr Gly Ile Ala Pro Val
            385                 390                 395                 400

Gly Phe Ala Gln His Val Thr Thr Gln Leu Val Leu Lys Asn Arg Gly
                            405                 410                 415

Val Tyr Glu Ser Val Lys Tyr Ile Gln Gln Glu Asn Phe Trp Ile Gly
                        420                 425                 430

Pro Ser Ser Ile Asp Leu Ile His Leu Gly Ala Lys Phe Ser Pro Cys
                        435                 440                 445

Ile Arg Lys Asp Gln Gln Ile Glu Gln Leu Val Arg Arg Glu Arg Asp
            450                 455                 460

Ile Glu Arg Thr Ser Gly Cys Cys Val Gln Asn Asp Arg Ser Gly Cys
            465                 470                 475                 480

Ile Gln Thr Leu Lys Lys Asp Cys Ser Glu Thr Leu Ala Thr Phe Val
                            485                 490                 495

Lys Trp Gln Asn Asp Thr Gly Pro Ser Asp Lys Ser Asp Leu Ser Gln
                        500                 505                 510

Lys Gln Pro Ser Ala Val Val Cys His Gln Asp Pro Arg Thr Cys Glu
                        515                 520                 525

Glu Pro Ala Ser Ser Gly Ala His Ile Trp Pro Asp Asp Ile Thr Lys
                    530                 535                 540

Trp Pro Ile Cys Thr Glu Gln Ala Gln Ser Asn His Thr Gly Leu Leu
            545                 550                 555                 560

His Ile Asp Cys Lys Ile Lys Gly Arg Pro Cys Cys Ile Gly Thr Lys
                            565                 570                 575
```

```
Gly Ser Cys Glu Ile Thr Thr Arg Glu Tyr Cys Glu Phe Met His Gly
            580                 585                 590

Tyr Phe His Glu Asp Ala Thr Leu Cys Ser Gln Val His Cys Leu Asp
            595                 600                 605

Lys Val Cys Gly Leu Leu Pro Phe Leu Asn Pro Glu Val Pro Asp Gln
            610                 615                 620

Phe Tyr Arg Ile Trp Leu Ser Leu Phe Leu His Ala Gly Ile Val His
625                 630                 635                 640

Cys Leu Val Ser Val Val Phe Gln Met Thr Ile Leu Arg Asp Leu Glu
            645                 650                 655

Lys Leu Ala Gly Trp His Arg Ile Ser Ile Ile Phe Ile Leu Ser Gly
            660                 665                 670

Ile Thr Gly Asn Leu Ala Ser Ala Ile Phe Leu Pro Tyr Arg Ala Glu
            675                 680                 685

Val Gly Pro Ala Gly Ser Gln Phe Gly Leu Leu Ala Cys Leu Phe Val
            690                 695                 700

Glu Leu Phe Gln Ser Trp Gln Leu Leu Glu Arg Pro Trp Lys Ala Phe
705                 710                 715                 720

Phe Asn Leu Ser Ala Ile Val Leu Phe Leu Phe Ile Cys Gly Leu Leu
            725                 730                 735

Pro Trp Ile Asp Asn Ile Ala His Ile Phe Gly Phe Leu Ser Gly Met
            740                 745                 750

Leu Leu Ala Phe Ala Phe Leu Pro Tyr Ile Thr Phe Gly Thr Ser Asp
            755                 760                 765

Lys Tyr Arg Lys Arg Ala Leu Ile Leu Val Ser Leu Leu Val Phe Ala
            770                 775                 780

Gly Leu Phe Ala Ser Leu Val Leu Trp Leu Tyr Ile Tyr Pro Ile Asn
785                 790                 795                 800

Trp Pro Trp Ile Glu Tyr Leu Thr Cys Phe Pro Phe Thr Ser Arg Phe
            805                 810                 815

Cys Glu Lys Tyr Glu Leu Asp Gln Val Leu His
            820                 825

<210> SEQ ID NO 3
<211> LENGTH: 20
<212> TYPE: DNA
<213> ORGANISM: Primer

<400> SEQUENCE: 3
gcaggctagc gtgttaaagg                                              20

<210> SEQ ID NO 4
<211> LENGTH: 19
<212> TYPE: DNA
<213> ORGANISM: Primer

<400> SEQUENCE: 4
aaaacggggt catagcagc                                               19

<210> SEQ ID NO 5
<211> LENGTH: 20
<212> TYPE: DNA
<213> ORGANISM: Primer

<400> SEQUENCE: 5
gcacatctga gggaaggaag                                              20
```

```
<210> SEQ ID NO 6
<211> LENGTH: 20
<212> TYPE: DNA
<213> ORGANISM: Primer

<400> SEQUENCE: 6
cttccggtca aatgcaaagt                                              20

<210> SEQ ID NO 7
<211> LENGTH: 600
<212> TYPE: DNA
<213> ORGANISM: Mus musculus

<400> SEQUENCE: 7
agcctacctg aagagtgtca gcctacagga gccccgggga cgatggcagg agggcgcaga    60
gaagcgcccc ggcttccgcc gccaggcctc cctgtcccag agcatccgca agagcacagc   120
ccagtggttt gggtcagcg cgactgggga gggcaagcga caaaactggc atcgtcgcag    180
cctgcaccac tgcagcgtgc actatggccg cctcaaggcc tcgtgccaga gagaactgga   240
gctgcccagc caggaggtgc catccttcca gggcactgag tctccaaaac cgtgcaagat   300
gcccaagatt gtggatccac tggctcgggg tagggccttc cgccatccag atgaggtgga   360
ccggcctcac gctgcccacc cacctctgac tccaggggtc ctgtctctca catccttcac   420
catgtccgct ctggctactc ccatctgccc cgccgcaaga ggatatctgt tgcccatatg   480
agctttcagg cagccgccgc cctcctcaag gggcgttccg tgctagatgc gactgggcag   540
cggtgccggc atgtcaaacg cagcttcgct taccccagct tcctggagga ggatgctgtc   600

<210> SEQ ID NO 8
<211> LENGTH: 19
<212> TYPE: DNA
<213> ORGANISM: Primer

<400> SEQUENCE: 8
actctgctct cagccgctt                                               19

<210> SEQ ID NO 9
<211> LENGTH: 20
<212> TYPE: DNA
<213> ORGANISM: Primer

<400> SEQUENCE: 9
ccagacacat gctggagcta                                              20

<210> SEQ ID NO 10
<211> LENGTH: 20
<212> TYPE: DNA
<213> ORGANISM: Primer

<400> SEQUENCE: 10
gcacatctga gggaaggaag                                              20

<210> SEQ ID NO 11
<211> LENGTH: 20
<212> TYPE: DNA
<213> ORGANISM: Primer

<400> SEQUENCE: 11
cttccggtca aatgcaaagt                                              20
```

```
<210> SEQ ID NO 12
<211> LENGTH: 600
<212> TYPE: DNA
<213> ORGANISM: Mus musculus

<400> SEQUENCE: 12
gtgtcagcct acaggagccc cggggacgat ggcaggaggg cgcagagaag cgccccggct      60
tccgccgcca ggcctccctg tcccagagca tccgcaagag cacagcccag tggtttgggg     120
tcagcggcga ctgggagggc aagcgacaaa actggcatcg tcgcagcctg caccactgca     180
gcgtgcacta tggccgcctc aaggcctcgt gccagagaga actggagctg cccagccagg     240
aggtgccatc cttccagggc actgagtctc caaaaccgtg caagatgccc aagattgtgg     300
atccactggc tcggggtagg gccttccgcc atccagatga ggtggaccgg cctcacgctg     360
cccacccacc tctgactcca ggggtcctgt ctctcacatc cttcaccatg tccgctctgg     420
ctactcccat ctgccccgcc gcaagaggat atctgttgcc catatgagct ttcaggcagc     480
cgccgccctc ctcaaggggc gttccgtgct agatgcgact gggcagcggt gccggcatgt     540
caaacgcagc ttcgcttacc ccagcttcct ggaggaggat gctgtcgatg gagctgacac     600

<210> SEQ ID NO 13
<211> LENGTH: 43
<212> TYPE: DNA
<213> ORGANISM: Primer

<400> SEQUENCE: 13
cggatccatg gcctcagctg acaagaatgg cagcaacctc cca                        43

<210> SEQ ID NO 14
<211> LENGTH: 34
<212> TYPE: DNA
<213> ORGANISM: Primer

<400> SEQUENCE: 14
ataaagcttg ctcgatctgg tccacgatgt gatt                                  34
```